US00RE45499E

(19) United States
(12) Reissued Patent
Schneider et al.

(10) Patent Number: US RE45,499 E
(45) Date of Reissued Patent: Apr. 28, 2015

(54) N-(2-AMINOPHENYL)-4-[N-(PYRIDINE-3-YL)-METHOXYCARBONYL-AMINO-METHYL]-BENZAMIDE (MS-275) POLYMORPH B

(71) Applicant: Bayer Intellectual Property GmbH, Monheim (DE)

(72) Inventors: Matthias Schneider, Potsdam (DE); Michael Gottfried, Wuppertal (DE); Jens Geisler, Berlin (DE); Gabriele Winter, Schoenfliess (DE); Joji Suzuki, Omuta (JP); Tomoyuki Ando, Omuta (JP); Masaru Honjo, Omuta (JP)

(73) Assignee: Bayer Intellectual Property GmbH, Monheim am Rhein (DE)

(21) Appl. No.: 14/201,684

(22) Filed: Mar. 7, 2014

Related U.S. Patent Documents

Reissue of:
(64) Patent No.: 7,973,166
Issued: Jul. 5, 2011
Appl. No.: 12/549,458
Filed: Aug. 28, 2009

U.S. Applications:
(60) Provisional application No. 61/093,046, filed on Aug. 29, 2008.

(30) Foreign Application Priority Data

Aug. 29, 2008 (EP) ..... 08163274

(51) Int. Cl.
*C07D 213/56* (2006.01)
*A01N 43/40* (2006.01)
*A61K 31/4406* (2006.01)

(52) U.S. Cl.
CPC ..... *A61K 31/4406* (2013.01)

(58) Field of Classification Search
None
See application file for complete search history.

(56) References Cited

FOREIGN PATENT DOCUMENTS

| | | | |
|---|---|---|---|
| EP | 0847992 | A1 | 9/1997 |
| EP | 0974576 | A2 * | 1/2000 |
| JP | 2001131130 | W | 5/2001 |
| WO | PCTEP2009006381 | R | 3/2009 |

OTHER PUBLICATIONS

Caira, M. R. "Crystalline Polymorphism of Organic Compounds" (Topics in Current Chemistry), 1998, 163-208, 198.

* cited by examiner

*Primary Examiner* — Heidi Reese
(74) *Attorney, Agent, or Firm* — Wilson Sonsini Goodrich & Rosati

(57) ABSTRACT

The crystalline Polymorph B of N-(2-aminophenyl)-4-[N-(pyridine-3-yl)methoxy-carbonyaminomethyl]benzamide (MS-275) of formula I (I)

is described, as well as the process for the production of said compound, and its use as a medicament for the treatment of selected diseases.

21 Claims, 14 Drawing Sheets

N-(2-AMINOPHENYL)-4-[N-(PYRIDINE-3-YL)-METHOXYCARBONYL-AMINO-METHYL]-BENZAMIDE (MS-275) POLYMORPH B

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application claims the benefit of the filing date of U.S. Provisional Application Ser. No. 61/093,046 filed Aug. 29, 2008, which is incorporated by reference herein.

The invention refers to the crystalline Polymorph B of N-(2-aminophenyl)-4-[N-(pyridine-3-yl)methoxycarbonylaminomethyl]benzamide (MS-275), the process for the production, and the use of said compound as a medicament for the treatment of selected diseases.

In EP 0 847 992 A1 (which co-patent is U.S. Pat. No. 6,794,392) benzamide derivatives as medicament for the treatment of malignant tumors, autoimmune diseases, dermatological diseases and parasitism are described. In particular, these derivatives are highly effective as anticancer drugs, preferred for the haematological malignancy and solid tumors. The preparation of N-(2-aminophenyl)-4-[N-(pyridine-3-yl)methoxycarbonylaminomethyl]-benzamide is described on page 57, Example 48. The compound is neither purified by chromatography nor purified by treatment with charcoal. The final step of the process comprises the recrystallization from ethanol.

Said compound has a melting point (mp) of 159-160° C.

The IR spectrum shows the following bands: IR(KBr) $cm^{-1}$: 3295, 1648, 1541, 1508, 1457, 1309, 1183, 742.

The data indicate the Polymorph A form.

In EP 0 974 576 B1 a method for the production of monoacylated phenylenediamine derivatives is described. The preparation of N-(2-aminophenyl)-4-[N-(pyridine-3-yl) methoxycarbonylamino-methyl]benzamide is described on pages 12 to 13, Example 6. The final step of the process comprises the purification of the compound via silica gel column chromatography.

Said compound has a melting point (mp) of 159-160° C.

The IR spectrum shows the following bands: IR(KBr) $cm^{-1}$: 3295, 1648, 1541, 1508, 1457, 1309, 1183, 742.

The data indicate the Polymorph A form.

In J. Med. Chem. 1999, 42, 3001-3003, the synthesis of new benzamide derivatives and the inhibition of histone deacetylase (HDAC) is described. The process for the production of N-(2-aminophenyl)-4-[N-(pyridine-3-yl)methoxycarbonylaminomethyl]benzamide is described. The final step of the process comprises the purification of the compound via silica gel column chromatography (ethyl acetate).

Said compound has a melting point (mp) of 159-160° C.

The IR spectrum shows the following bands: IR(KBr) $cm^{-1}$: 3295, 1648, 1541, 1508, 1457, 1309, 1183, 742.

The data indicate the Polymorph A form.

In WO 01/12193 A1 a pharmaceutical formulation comprising N-(2-aminophenyl)-4-[N-(pyridine-3-yl)methoxycarbonylamino-methyl]benzamide is described.

In WO 01/16106 a formulation comprising N-(2-aminophenyl)-4-[N-(pyridine-3-yl)methoxycarbonylamino-methyl]benzamide, having an increased solubility and an improved oral absorption for benzamide derivatives, and pharmaceutically acceptable salts thereof are described.

In WO 2004/103369 a pharmaceutical composition is described which comprises histone deacetylase inhibitors. That application concerns the combined use of N-(2-aminophenyl)-4-[N-(pyridine-3-yl)methoxycarbonylamino-methyl]benzamide together with different cancer active compounds. In fact that application is a later application, which is based on the above mentioned matter and thus concerns the Polymorph A form.

Finally, JP 2001-131130 (11-317580) describes a process for the purification of monoacylphenylenediamine derivatives. In Reference Example 2, the process for the production of crude N-(2-aminophenyl)-4-[N-(pyridine-3-yl)meth-oxycarbonylaminomethyl]benzamide is described.

Said compound has a melting point (mp) of 159-160° C.,

The IR spectrum shows the following bands: IR(KBr) $cm^{-1}$: 3295, 1648, 1541, 1508, 1457, 1309, 1183, 742.

The data indicate the Polymorph A form.

Moreover, Working Example 1 describes the purification of crude N-(2-aminophenyl)-4-[N-(pyridine-3-yl)methoxycarbonylaminomethyl]benzamide in aqueous acid medium together with carbon. The final crystallization is done under aqueous conditions at 40-50° C.

Following the description to that example it can be seen from the Comparative Examples 1-3 that the crude N-(2-aminophenyl)-4-[N-(pyridine-3-yl)meth-oxycarbonylaminomethyl]benzamide is not purified by dissolution under reflux conditions in either ethanol, methanol or acetonitrile followed by a recrystallization at 2° C. As a result, these recrystallizations do not yield any pure compound.

In addition a "purification" of crude N-(2-aminophenyl)-4-[N-(pyridine-3-yl)methoxycarbonylaminomethyl]benzamide in ethanol under reflux conditions together with carbon is described. After filtering off the carbon the compound is recrystallized at 2° C. The purification effect of this method is very limited. 1.1% of an impurity remain in the N-(2-aminophenyl)-4-[N-(pyridine-3-yl)methoxycarbonylaminomethyl]benzamide. As a result, this procedure does not yield any pure compound.

None of the state of the art documents refer to a polymorph B of N-(2-aminophenyl)-4-[N-(pyridine-3-yl)methoxycarbonylamino-methyl]benzamide and no physicochemical features of said compound are known.

Several biological and clinical studies have been done with N-(2-aminophenyl)-4-[N-(pyridine-3-yl)meth-oxycarbonylaminomethyl]benzamide. For example, Kummar et al., Clin Cancer Res. 13 (18), 2007, pp 5411-5417 describe a phase I trial of N-(2-aminophenyl)-4-[N-(pyridine-3-yl)meth-oxycarbonylaminomethyl]benzamide in refractory solid tumors. The compound was applied orally.

A further study in advanced refractory solid tumors or lymphoma was published by Ryan et al., J. Clin. Oncol., Vol. 23, 17, 2005, pp. 3912-3922 and Gore et al., Clin Cancer Res., Vol 14, 2008, pp. 4517-4525.

Further activity in adults with refractory and relapsed acute leukemias are published by Gojo et al., Blood, Vol. 109, 2007, pp. 2781-2790.

In the course of process development (scale up and modified purification process) it has now surprisingly been found that the known form of N-(2-aminophenyl)-4-[N-(pyridine-3-yl)methoxycarbonylamino-methyl]benzamide which is described in the above mentioned state of the art, is not the thermodynamically stable polymorph of said compound, at least not in the relevant temperature range below 60° C., but is polymorph A of N-(2-aminophenyl)-4-[N-(pyridine-3-yl) methoxycarbonylamino-methyl]benzamide.

This generates problems of not using the thermodynamically stable polymorph of N-(2-aminophenyl)-4-[N-(pyridine-3-yl)methoxycarbonylaminomethyl]benzamide for drug development when using polymorph A. This bears for example the risk that the polymorph A form of N-(2-aminophenyl)-4-[N-(pyridine-3-yl)methoxycarbonylamino-methyl]benzamide transforms partly or completely into other polymorph forms of N-(2-aminophenyl)-4-[N-(pyridine-3-yl)methoxycarbonylamino-methyl]benzamide (e.g. during storage as drug substance as well as drug product). However, a stable solid state form is a prerequisite for developing a medicinal product because a conversion of the solid form is associated with changes in properties.

In addition, it was not possible to establish a reliable manufacturing process for polymorph A as pure polymorphic phase at larger scale.

An additional problem is the reliable manufacture of polymorph A with high chemical purity.

These problems are now solved by the thermodynamically more stable polymorph of N-(2-aminophenyl)-4-[N-(pyridine-3-yl)methoxycarbonylamino-methyl]-benzamide, polymorph B, as described herein.

The inventive N-(2-aminophenyl)-4-[N-(pyridine-3-yl) methoxy-carbonylamino-methyl]benzamide polymorph B of formula I (I)

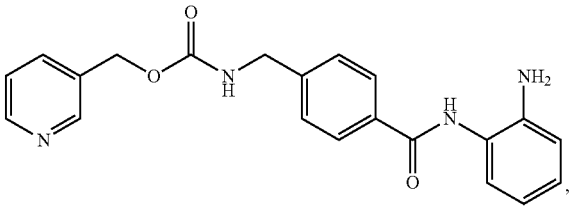

can be obtained via a process, which comprises the following process steps:

a) crude N-(2-aminophenyl)-4-[N-(pyridine-3-yl)methoxycarbonylaminomethyl]-benzamide is dissolved in water and diluted hydrochloric acid is added to the reaction mixture, at a constant internal reaction vessel temperature below 5° C., and b) to said reaction mixture charcoal is added and the reaction mixture is then stirred for 1 to 20 hours at a constant temperature below 5° C., and c) is filtered to remove the charcoal from the solution and is rinsed with water, and d) while keeping the internal vessel temperature below 5° C. the pH of the reaction mixture is adjusted to ≥8 with a diluted sodium hydroxide solution, and e) the resulting precipitated N-(2-aminophenyl)-4-[N-(pyridine-3-yl)methoxycarbonylaminomethyl]-benzamide is washed with water and ethanol, and is dried, and f) the precipitate is suspended into a mixture of ethanol and water and is heated up to a temperature of 40-90° C. for 1 to 10 hours, and g) after cooling down the mixture, the resulting precipitate is rinsed with water and ethanol to give the pure N-(2-aminophenyl)-4-[N-(pyridine-3-yl)methoxycarbony-laminomethyl]-benzamide polymorph B which is subsequently dried at a temperature between 30-60° C.

The inventive process is also an object of the instant invention

The crude N-(2-aminophenyl)-4-[N-(pyridine-3-yl)methoxycarbonylaminomethyl]-benzamide of step a) can be produced according to the method described in example 6 of EP 0974 576 B1.

The inventive N-(2-aminophenyl)-4-[N-(pyridine-3-yl) methoxycarbonylamino-methyl]-benzamide polymorph B, produced according to the instant process might have a chemically purity of at least 94%, preferred of at least 96%, more preferred of at least 98%, much more preferred of at least 99%, most preferred of at least 99.5%.

It should be noted that the inventive N-(2-aminophenyl)-4-[N-(pyridine-3-yl)methoxycarbonylamino-methyl]-benzamide polymorph B is free of any Polymorph A form.

For example, a higher purity can be achieved by repeating step b) and step c) of the above mentioned process if after passing step c), an insufficient purity of the N-(2-aminophenyl)-4-[N-(pyridine-3-yl)methoxycarbonylamino-methyl]-benzamide is determined.

One embodiment provides for polymorph B of N-(2-aminophenyl)-4-[N-(pyridine-3-yl)methoxycarbonylamino-methyl]benzamide substantially free of any other solid state form (e.g., another polymorph).

A further embodiment provides for polymorph B of N-(2-aminophenyl)-4-[N-(pyridine-3-yl)methoxycarbonylaminomethyl]benzamide substantially free of polymorph A of N-(2-aminophenyl)-4-[N-(pyridine-3-yl)methoxycarbony-lamino-methyl]benzamide.

As referred to herein, the term "substantially free" includes a solid state composition completely free of other solid state forms of N-(2-aminophenyl)-4-[N-(pyridine-3-yl)methoxycarbonylamino-methyl]benzamide. The term "substantially free" also includes solid state compositions of polymorph B that contain less than 10%, less than 5%, less than 2%, less than 1%, or less than 0.5% of other solid state forms or other polymorphs; wherein the content of other form of N-(2-aminophenyl)-4-[N-(pyridine-3-yl)methoxycarbonylaminomethyl]benzamide is determined by various analytical methods, e.g. X-ray powder diffraction, FT-Raman spectroscopy, IR spectroscopy, differential scanning calorimetry, microcalorimetry and solid state NMR.

In addition to polymorph B of N-(2-aminophenyl)-4-[N-(pyridine-3-yl)methoxycarbonyl-aminomethyl]benzamide, a third anhydrous form, the poly-morph C of N-(2-aminophenyl)-4-[N-(pyridine-3-yl)methoxycarbo-nylamino-methyl]-benzamide and an amorphous phase were found.

The polymorph C and the amorphous phase of N-(2-aminophenyl)-4-[N-(pyridine-3-yl)methoxycarbo-nylaminomethyl]-benzamide are thus also an object of the invention.

The polymorph B of N-(2-aminophenyl)-4-[N-(pyridine-3-yl)methoxycarbonyl-aminomethyl]benzamide is an anhydrous form and has a melting point (mp) of 156-158° C. (see Example 2).

The polymorph C of N-(2-aminophenyl)-4-[N-(pyridine-3-yl)methoxycarbo-nylamino-methyl]-benzamide is characterized by its melting point of 152-155° C. The amorphous phase is characterized by a glass transition temperature between 30° C. and 50° C. Depending on heating rate the amorphous phase recrystallizes during heating into one of the polymorphs.

Beside the melting points, polymorph A, polymorph B and polymorph C are also be distinguishable by the positions of the reflections in the X-ray powder diffraction (XRPD) pattern (see Example 3). The amorphous phase is characterized by the a X-ray powder diffraction pattern which shows only one or two broad diffuse maxima, but no defined XRPD reflections.

The three different polymorphs, as well as the amorphous phase, can further be distinguished by their characteristic bands in the FT-Raman spectra (see Example 4).

A differentiation between the present state of the art, polymorph A, and the new polymorph B of N-(2-aminophenyl)-4-[N-(pyridine-3-yl)methoxycarbonylamino-methyl]-benzamide is also possible by IR spectroscopy (see Example 5).

The polymorph B is the thermodynamically stable polymorph of N-(2-aminophenyl)-4-[N-(pyridine-3-yl)methoxycarbonylaminomethyl]-benzamide at least in the relevant temperature range below 600, which is therefore the preferred form for the use as medicament.

Thus, the crystalline N-(2-aminophenyl)-4-[N-(pyridine-3-yl)methoxycarbonyl-amino-methyl]-benzamide polymorph B is characterized in that its X-ray diffractogram has a reflection at 2Theta=21.1°.

Further, the crystalline N-(2-aminophenyl)-4-[N-(pyridine-3-yl)methoxycarbonyl-amino-methyl]-benzamide polymorph B is characterized in that its X-ray diffractogram has reflections at 2Theta=21.1°, 20.4° and 27.4°.

Additional characterization is given by the Raman spectrum, wherein the crystalline N-(2-aminophenyl)-4-[N-(pyridine-3-yl)methoxycarbonylamino-methyl]-benzamide polymorph B has its a bands at 902 $cm^{-1}$, 3036 $cm^{-1}$, 1639 $cm^{-1}$ and 916 $cm^{-1}$.

The IR-spectrum of polymorph B of N-(2-aminophenyl)-4-[N-(pyridine-3-yl-methoxycarbonylamino-methyl]-benzamide shows the following characteristic bands: IR (KBr) $cm^{-1}$::3349, 3311, 1705, 1641, 1262 and 751. and IR (ATR) $cm^{-1}$: 3349, 3309, 1702, 1638, 1260 and 749.

Thus, the characteristics of the pure crystalline N-(2-aminophenyl)-4-[N-(pyridine-3-yl)methoxycarbonylamino-methyl]-benzamide polymorph B are its X-ray diffractogram which has a reflection at 2Theta=21.1°, 20.4° and 27.4°, and its FT-Raman spectrum which has bands at 1705 $cm^{-1}$, 1641 $cm^{-1}$, 1262 $cm^{-1}$ and 751 $cm^{-1}$, and its IR (ATR) spectrum with bands at 1702 $cm^{-1}$, 1638 $cm^{-1}$, 1260 $cm^{-1}$ and 749 $cm^{-1}$ Due to the fact that the polymorph B is the thermodynamically stable polymorph of MS-275, at least in the relevant temperature range below 600, its manufacture in highly pure form at larger scale is easier than the manufacture of polymorph A of MS-275.

The N-(2-aminophenyl)-4-[N-(pyridine-3-yl)methoxycarbonylaminomethyl]-benzamide polymorph B can be used for the production of a medicament for the treatment of different diseases, as well as in established test systems.

For example, N-(2-aminophenyl)-4-[N-(pyridine-3-yl) methoxycarbonylamino-methyl]benzamide polymorph B can be used as medicament for the treatment of malignant tumors, auto-immune diseases, dermatological diseases and parasitism.

The term "malignant tumors" comprises hematologic malignancy such as acute leukaemia, malignant lymphoma, multiple myeloma and macroglobulinemia as well as solid tumors such as colon cancer, cerebral tumor, head and neck tumor, breast carcinoma, pulmonary cancer, oesophageal cancer, gastric cancer, hepatic cancer, gallbladder cancer, bile duct cancer, pancreatic cancer, nesidioblastoma, renal cell carcinoma, adrenocortical cancer, urinary bladder carcinoma, prostatic cancer, testicular tumor, ovarian carcinoma, uterine cancer, chorionic carcinoma, thyroid cancer, malignant carcinoid tumor, skin cancer, malignant melanoma, osteogenic sarcoma, soft tissue sarcoma, neuroblastoma, Wilms tumor and retinoblastoma.

The term "autoimmune diseases" comprises rheumatism, diabetes, systemic lupus erythematodes, human autoimmune lymphocytic lymphadenopathy, immunoblastic lymphadenopathy, Crohn disease and ulcerative colitis.

The term "dermatologic diseases" comprises psoriasis, acne, eczema and atopic dermatitis.

The term "parasitism" includes diseases such as malaria caused through vermination.

The invention thus further comprises the use of N-(2-aminophenyl)-4-[N-(pyridine-3-yl)methoxycarbonylamino-methyl]-benzamide polymorph B for the treatment of said diseases, as well as the use of N-(2-aminophenyl)-4-[N-(pyridine-3-yl)methoxycarbonylamino-methyl]-benzamide polymorph B for the production of a medicament for the treatment of said diseases.

The use of N-(2-aminophenyl)-4-[N-(pyridine-3-yl)methoxycarbonylamino-methyl]-benzamide polymorph B as medicament for the treatment of malignant tumors is preferred.

The manufacture of the medicaments/formulations may be performed according to methods known in the art. Commonly known and used adjuvants, as well as further suitable carriers or diluents may be used.

Suitable carriers and adjuvants may be such as recommended for pharmacy, cosmetics and related fields in: Ullmann's Encyclopedia of Technical Chemistry, Vol. 4, (1953), pp. 1-39; Journal of Pharmaceutical Sciences, Vol. 52 (1963), p. 918ff; H. v. Czetsch-Lindenwald, "Hilfsstoffe für Pharmazie and angrenzende Gebiete"; Pharm. Ind. 2, 1961, p. 72ff; Dr. H. P. Fiedler, Lexikon der Hilfsstoffe für Pharmazie, Kosmetik und angrenzende Gebiete, Cantor K G, Aulendorf in Württemberg, 1971, which are hereby incorporated by reference.

Said medicaments and formulations are also an object of the instant invention.

For a therapeutical effect the sensible dose is different and depends on the concentration in the pharmaceutical composition, the host, the form of application and the intensity of the disease which is treated.

The invention also comprises pharmaceutical compositions, which can be prepared by known methods of preparing galenics for oral, enteral, parenteral, e.g. intravenous, intraperitoneal, intramuscular, subcutaneous or percutaneous application. The inventive combination can also be implanted into tissue. Thus, the invention comprises the use of the N-(2-aminophenyl)-4-[N-(pyridine-3-yl)methoxycarbonylaminomethyl]-benzamide polymorph B composition for enteral administration, such as nasal, buccal, rectal or, especially, oral administration, and for parenteral administration, such as intravenous, intramuscular or subcutaneous administration, to warm-blooded animals, especially, humans, are especially preferred. The compositions comprise the N-(2-aminophenyl)-4-[N-(pyridine-3-yl)methoxycarbonylamino-methyl]-benzamide polymorph B alone or, preferably, together with a pharmaceutically acceptable diluent and/or carrier. The dosage of the active ingredient depends upon the disease to be treated and upon the species, gender, age, weight, and individual condition, the individual pharmacokinetic data, and the mode of administration.

Preferred amounts of N-(2-aminophenyl)-4-[N-(pyridine-3-yl)methoxycarbonylaminomethyl]-benzamide polymorph B are in the range of 0.0001 to 100 mg/kg per day, preferred 0.001 to 10 mg/kg per day, more preferred 0.01 to 1 mg/kg per day and most preferred 0.05 to 0.5 mg/kg per day.

Depending on the amount, necessary for the treatment of a patient it might be useful to apply a defined amount of active compound on one or on several days in the same or different dose.

N-(2-aminophenyl)-4-[N-(pyridine-3-yl)methoxycarbonyl-aminomethyl]-benzamide polymorph B can also be used prophylactically or especially therapeutically, to a process for the preparation of a composition (especially in the form of compositions for the treatment of tumors) and to a method of treating of a number of diseases, especially tumor diseases, more especially those mentioned hereinabove.

In the preferred embodiment, the N-(2-aminophenyl)-4-[N-(pyridine-3-yl)methoxycarbonyl-aminomethyl]-benzamide polymorph B is suitable for administration to a warm-blooded animal, especially humans or commercially useful mammals suffering form a disease especially a neoplastic disease, and comprises an effective quantity of said compound for the treatment of the disease, together with at least one pharmaceutically acceptable carrier.

The N-(2-aminophenyl)-4-[N-(pyridine-3-yl)methoxycarbonyl-aminomethyl]-benzamide polymorph B can also be administered in the form of tablets, film coated tablets, wafers, suppositories, pills, dragees, gel capsules, granules, suppositories, implants, injectable sterile aqueous or oily solutions, suspensions or emulsions, ointments, creams, gels, patches for transdermal administration, formulations suitable for administration by inhalation, for instance nasal sprays.

As combination with at least one pharmaceutically acceptable carrier, said combination comprises the N-(2-aminophenyl)-4-[N-(pyridine-3-yl)methoxycarbonylaminomethyl]-benzamide polymorph B from approximately 0.1% to approximately 95%, single-dose administration forms comprising in the preferred embodiment from approximately 1% to approximately 20% active ingredient. Unit dose forms are, for example, coated and uncoated tablets, ampoules, vials, suppositories or capsules. Further dosage forms are, for example, ointments, creams, pastes, foams, tinctures, lipsticks, drops, sprays, dispersions, etc. Examples are capsules containing from about 0.05 mg to about 1.0 g active ingredients.

For the preparation of the pharmaceutical compositions for oral administration, the active agents suitable for the purposes of the present invention as defined above can be admixed with commonly known and used adjuvants and carriers such as for example, gum arabic, talcum, starch, sugars like e.g. mannitose, methyl cellulose, lactose, gelatin, surface-active agents, magnesium stearate, aqueous or non-aqueous excipients, paraffin derivatives, crosslinking agents, dispersants, emulsifiers, lubricants, conserving agents and flavoring agents (e.g., ethereal oils).

In the pharmaceutical composition, the N-(2-aminophenyl)-4-[N-(pyridine-3-yl)methoxycarbonyl-aminomethyl]-benzamide polymorph B may be dispersed in a microparticle, e.g. a nanoparticulate, composition.

The N-(2-aminophenyl)-4-[N-(pyridine-3-yl)methoxycarbonylaminomethyl]-benzamide polymorph B can thus be combined with one or more of those physiologically acceptable pharmaceutical adjuvants and carriers to give an acceptable formulation as medicament.

Further pharmacologically effective adjuvants and carriers are, for example, described in Remington's Pharmaceutical Science, 15$^{th}$ ed. Mack Publishing Company, Easton Pa. (1980), which is hereby incorporated by reference In order to further enhance the bioavailability of the N-(2-aminophenyl)-4-[N-(pyridine-3-yl)methoxycarbonylaminomethyl]-benzamide polymorph B, the compound suitable for the purposes of the present invention as defined above can also be formulated as cyclodextrin clathrates by reacting them with α-, β- or γ-cyclodextrines or derivatives thereof according to the method as disclosed in WO 96/02277.

For parenteral administration the N-(2-aminophenyl)-4-[N-(pyridine-3-yl)methoxycarbonylamino-methyl]-benzamide polymorph B suitable for the purposes of the present invention as defined above can be dissolved or suspended in a physiologically acceptable diluent, such as e.g., oils with or without solubilizers, surface-active agents, dispersants or emulsifiers. As oils for example and without limitation, olive oil, peanut oil, cottonseed oil, soybean oil, castor oil and sesame oil may be used.

The N-(2-aminophenyl)-4-[N-(pyridine-3-yl)methoxycarbonylaminomethyl]-benzamide polymorph B according to the present invention can also be administered via a depot injection or an implant preparation, optionally for sustained delivery of the active agent(s).

Implants can comprise as inert materials e.g. biologically degradable polymers or synthetic silicones such as e.g. silicone rubber.

For percutaneous applications, the N-(2-aminophenyl)-4-[N-(pyridine-3-yl)methoxycarbonylamino-methyl]-benzamide polymorph B may also be formulated into adhesives.

The preferred mode of administration is oral administration.

Formulations comprising the N-(2-aminophenyl)-4-[N-(pyridine-3-yl)methoxycarbonylaminomethyl]-benzamide polymorph B can be prepared in a manner known per se, for example by means of conventional mixing, granulating, coating, dissolving or lyophilizing processes.

Preference is given to the use of solutions of the N-(2-aminophenyl)-4-[N-(pyridine-3-yl)methoxycarbonylaminomethyl]-benzamide polymorph B, and also suspensions or dispersions, especially isotonic aqueous solutions, dispersions or suspensions which, for example in the case of lyophilized compositions comprising the active ingredients alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise visosity-increasing agents, typically sodium carboxymethylcellulose, carboxymethylcellulose, dextran, polyvinylpyrrolidone, or gelatins, or also solubilizers, for example Tween 80 [polyoxyethylene(20)sorbitan mono-oleate; trademark (®) of ICI Americas, Inc. USA].

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, expecially from 12 to 22, carbon atoms, for example lauric acid, tripdecylic acid, myristic acid, pentadecylic acid, palmitic acid, margaric acid, stearic acid, arachidic acid, behenic acid or corresponding unsaturated acids, for example oleaic acid, elaidic acid, erucic acid, brassidic acid or linoleic acid, if desired with the addition of anti-oxidants, for example vitamin E, β-carotene or 3,5-di-tert-butyl-4-hydroxytoluene. The alcohol component of these fatty acid esters has a maximum of 6 carbon atoms and is a monovalent or polyvalent, for example a mono-, di- or trivalent, alcohol, for example methanol, ethanol, propanol, butanol or pentanol or the isomers thereof, but especially glycol and glycerol. As fatty acid esters, therefore, the following are mentioned: ethyl oleate, isopropyl myristate, isopropyl palmitate, "Labrafil M 2375"® (polyoxyethylene glycerol trioleate from Gattefossé, Paris), "Labrafil M 1944 CS"® (unsaturated polyglycolized glycerides prepared by alcoholysis of apricot kernel oil and consisting of glycerides and polyethylene glycol ester; Gattefossé, France), "Labrasor"® (saturated polyglycolized glycerides prepared by alcoholysis of TCM and consisting of glycerides and polyethylene glycol ester; Gattefossé, France), and/or "Miglyol 812"® (triglyceride of saturated fatty acids of chain length $C_8$ to $C_{12}$ from Hüls AG, Germany), but especially vegetable oils such as cottonseed oil, almond oil, olive oil, castor oil, sesame oil, soybean oil and more expecially groundnut oil.

The manufacture of injectable preparations is usually carried out under sterile conditions, as is filling, for example into ampoules or vials, and the sealing of the containers.

Pharmaceutical compositions for oral administration can be obtained, for example, by combining the N-(2-aminophenyl)-4-[N-(pyridine-3-yl)methoxycarbonyl-aminomethyl]-benzamide polymorph B with one or more solid carriers, if desired granulating a resulting mixture, and processing the mixture of granules, if desired or necessary, by the inclusion of additional excipients, to form tablets or tablet cores.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methyl-cellulose, hydroxypropyl methylcellulose, sodium carboxymethyl-cellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of inter alia, concentrated sugar solutions, which may comprise gum arabic, talc, polyvinylpyrrolidone, polyethylene glycol and/or titanium dioxide, or coating solutions in suitable organic solvents or solvent mixture, or for the preparation of enteric coatings, solutions of suitable cellulose preparations, such as acetyl cellulose phthalate or hydroxypropylmethylcellulose phthalate. Dyes or pigments may be added to the tablets or tablet coatings, for example for identification purposes or to indicate different doses of the N-(2-aminophenyl)-4-[N-(pyridine-3-yl)methoxycarbonylaminomethyl]-benzamide polymorph B.

Pharmaceutical compositions for oral administration also include hard capsules consisting of gelatin, and also soft, sealed capsules consisting of gelatin and plasticizer, such as glycerol or sorbitol. The hard capsules may contain the N-(2-aminophenyl)-4-[N-(pyridine-3-yl)methoxycarbonylaminomethyl]-benzamide polymorph B in the form of granules, for example in admixture with fillers, such as corn starch, binders, and/or glidants, such as talc or magnesium stearate, and optionally stabilizers. In soft capsules, the N-(2-aminophenyl)-4-[N-(pyridine-3-yl)methoxycarbonylaminomethyl]-benzamide polymorph B is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Other oral dosage forms are, for example syrups prepared in customary manner which comprise the active ingredient, for example, in suspended form and in a concentration of about 5% to 20%, preferably about 10%, or in similar concentration that provides a suitable single dose, for example, when administered in measures of 5 or 10 ml. Also suitable are, for example, powdered or liquid concentrates for the preparation of shakes, for example in milk. Such concentrates may also be packaged in single-dose units.

Pharmaceutical compositions suitable for rectal administration are, for example, suppositories that consist of a combination of the N-(2-aminophenyl)-4-[N-(pyridine-3-yl)methoxycarbonylaminomethyl]-benzamide polymorph B and a suppository base. Suitable suppository bases are, for example, natural or synthetic triglycerides, paraffin hydrocarbons, polyethylene glycols or higher alkanols.

For parenteral administration. aqueous solutions of the N-(2-aminophenyl)-4-[N-(pyridine-3-yl)methoxycarbonylaminomethyl]-benzamide polymorph B in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The N-(2-aminophenyl)-4-[N-(pyridine-3-yl)methoxycarbonyl-aminomethyl]-benzamide polymorph B, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or micro-bicides, such as sorbic acid or benzoic acid.

The present invention relates especially also to the use of the combination, as such or in the form of a pharmaceutical formulation with at least one pharmaceutically acceptable carrier for the therapeutic and also prophylactic management of one or more of the diseases mentioned hereinabove, especially a neoplastic disease.

Optionally, the N-(2-aminophenyl)-4-[N-(pyridine-3-yl)methoxycarbonylamino-methyl]-benzamide polymorph B can be combined with one or more pharmacologically active agents.

For example, the compounds of this invention can be combined with known anti-hyper-proliferative, antiinflammatory, analgesic, immunoregulatory, diuretic, antiarrhythmic, anti-hypercholesterolemia, anti-dyslipidemia, anti-diabetic or antiviral agents, and the like, as well as with admixtures and combinations thereof.

A combination of the N-(2-aminophenyl)-4-[N-(pyridine-3-yl)methoxycarbonyl-amino-methyl]-benzamide polymorph B together with cytotoxic agents is preferred.

The additional pharmaceutical agent can be aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin (exemestan), 5-azacytidine, azathioprine, BCG or twice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, 2-cladribine, clodronic acid, cyclophosphamide, cytarabine, dacarbazine, dactinomycin, DaunoXome, decadron, decadron phosphate, delestrogen, denileukin diftitox, depomedrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, erlotinib (Tarceva), estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzamab, gleevec, gliadel, goserelin, granisetron HCl, histrelin, hycamtin, hydrocortone, eyrthrohydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulphate, letrozole, leucovorin, leuprolide, leuprolide acetate, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, rebiff, rhenium-186 etidronate, rituximab, roferon-A, romurtide, salagen, sandostatin, sargramostim, semustine, sizofuran, sobuzoxane, solumedrol, sparfosic acid, stem-cell therapy, streptozocin, strontium-89 chloride, synthroid, tamoxifen, tamsulosin, tasonermin, testolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, BAY 43-9006 (sorafenib), avastin, CCl-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MIP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

The additional pharmaceutical agent can also be gemcitabine, paclitaxel, cisplatin, carboplatin, sodium butyrate, 5-FU, doxorubicin, tamoxifen, etoposide, trastumazab, gefitinib, intron A, rapamycin, 17-AAG, U0126, insulin, an insulin derivative, a PPAR ligand, a sulfonylurea drug, an α-glucosidase inhibitor, a biguanide, a PTP-1 B inhibitor, a DPP-IV inhibitor, a 11-beta-HSD inhibitor, GLP-1, a GLP-1 derivative, GIP, a GIP derivative, PACAP, a PACAP derivative, secretin or a secretin derivative.

Optional anti-hyper-proliferative agents which can be added to the composition include but are not limited to compounds listed on the cancer chemotherapy drug regimens in the 11$^{th}$ Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

It should be noted that some of the above mentioned compounds are trademarks (®).

Generally, the use of cytotoxic and/or cytostatic agents in combination with the N-(2-aminophenyl)-4-[N-(pyridine-3-yl)methoxycarbonyl-amino-methyl]-benzamide polymorph B of the present invention will serve to:

i) yield better efficacy in reducing the growth of a tumor or even eliminate the tumor as compared to administration of either agent alone,
ii) provide for the administration of lesser amounts of the administered chemotherapeutic agents,
iii) provide for a chemotherapeutic treatment that is well tolerated in the patient with fewer deleterious pharmacological complications than observed with single agent chemotherapies and certain other combined therapies,
iv) provide for treating a broader spectrum of different cancer types in mammals, especially humans,
v) provide for a higher response rate among treated patients,
vi) provide for a longer survival time among treated patients compared to standard chemotherapy treatments,
vii) provide a longer time for tumor progression, and/or yield efficacy and tolerability results at least as good as those of the agents used alone, compared to known instances where other cancer agent combinations produce antagonistic effects.

The instant invention further comprises the combination of the N-(2-amino-phenyl)-4-[N-(midine-3-yl)methoxycarbonylamino-methyl]-benzamide polymorph B together with one or more regiments of cytotoxic agents, for example, Folfox4 (fluorouracil/leucovorin/oxaliplatin); Folfiri (leukovorin, 5-fluorouracil, irinotecan); DHAP (cisplatin/cytarabine/dexamethasone), CEOP (cyclophosphamide/epirubicin/vincristine/prednisone), CHOP (cyclophosphamide, doxorubicin, vincristine and prednisone), FLAG (fludarabine/cytarabine/filgrastim), M & P (mitoxantrone+prednisone; or melphalan+prednisone) ABMC (doxorubicin/carmustine/melphalan/cyclophosphamide), ICE (ifosfamide, carboplatin and etoposide), DVP (daunorubicin, vincristine and prednisone), ATRA (all-trans retinoic acid), ABVD (bleomycin, dacarbazin, doxorubicin and vincristine), COP (cyclophosphamide, vincristine and prednisone), VAD (vincristine, adriamycin and dexamethasone) and MOPP (mechlorethamine, prednisone, procabazine and vincristine).

The cytotoxic agents itself or from the regimens are either commercially available or can be prepared by standard literature procedures.

The N-(2-aminophenyl)-4-[N-(pyridine-3-yl)methoxycarbonylaminomethyl]-benzamide polymorph B can be applied in an pharmaceutically effective amount together with one or more of these cytotoxic agents simultaneously, separately or sequentially.

The amounts (a "pharmaceutically effective amount") of the combined active agents to be administered vary within a broad range and depend on the condition to be treated and the mode of administration. They can cover any amount efficient for the intended treatment. Determining a "pharmaceutically effective amount" of the combined active agent is within the purview of a person skilled in the art.

Those combinations which comprise the N-(2-aminophenyl)-4-[N-(pyridine-3-yl)methoxy-carbonylaminomethyl]-benzamide polymorph B together with cytotoxic and/or cytostatic agents are also matter of the instant invention.

EXAMPLES

Example 1

Process for the Production of N-(2-aminophenyl)-4-[N-(pyridine-3-yl)-methoxycarbonylaminomethyl]-benzamide, Polymorph B Form 30 kg of crude N-(2-aminophenyl)-4-[N-(pyridine-3-yl) methoxycarbonylaminomethyl]-benzamide (MS-275, crude) was transferred into a reaction vessel and approximately 300 kg of water have been added. To that reaction mixture approximately 18 kg of hydrochloric acid, 36% (w/w), diluted in approximately 66 kg of water, have been added, while keeping the internal temperature constantly below 5° C. Under control of the internal temperature, 15 kg charcoal was added and the reaction mixture was stirred for approximately 10 hours.

After that reaction time the reaction solution was filtered to remove the charcoal from the solution and was accordingly rinsed with approximately 90 kg of water.

The purity of N-(2-aminophenyl)-4-[N-(pyridine-3-yl) methoxycarbonylamino-methyl]-benzamide was determined. If the purity was insufficient, again 15 kg charcoal was added to the filtrate and stirred for further 10 hours, and again the reaction solution was filtered to remove the charcoal from the solution and was accordingly rinsed with approximately 90 kg of water.

While keeping the internal temperature below 5° C. the pH of the reaction mixture was adjust to ≥8 by using a diluted sodium hydroxide solution. After said treatment the N-(2-aminophenyl)-4-[N-(pyridine-3-yl)methoxycarbonylaminomethyl]-benzamide product, which has been precipitated, was washed with approximately 120 kg water and with approximately 68 kg ethanol.

The precipitate was then dried at a temperature between 30-60° C. After the precipitate was dried, it was suspended in a mixture of 5-fold (e.g. approximately 63 kg) ethanol and of 7-fold (e.g. approximately 111 kg) water, and was heated up to 40-90° C. for 5 hours. After that reaction time the reaction mixture was cooled down. The precipitate was rinsed with approximately 120 kg of water and with approximately 52 kg of ethanol.

The N-(2-aminophenyl)-4-[N-(pyridine-3-yl)methoxycarbonylaminomethyl]-benzamide product was dried at a temperature between 30-60° C.

Yield: 9 kg-24 kg (30%-80% of theory)

Melting Point: 156-158° C.

Example 2

Analysis of the N-(2-aminophenyl)-4-[N-(pyridine-3-yl)methoxycarbonyl-aminomethyl]-benzamide Polymorphs and of the Amorphous Phase by Differential Scanning calorimetry (DSC)

The DSC traces were recorded with a heating rate of 5 K/min in aluminium pans under nitrogen atmosphere. The determined melting temperatures of the three polymorphs are given in the following Table 1.

TABLE 1

| Polymorph A | Polymorph B | Polymorph C |
|---|---|---|
| 160° C. ± 1K | 157° C. ± 1K | 152° C.-155° C. |

According to a person ordinary skilled in the art, the determined melting temperature depends on the experimental conditions, especially on the used heating rate. In addition, the melting temperature is influenced by the chemical purity of the material. The reported melting temperature were determined on batches with a purity of at least 98.5%.

Example 3

Analysis of the N-(2-aminophenyl)-4-[N-(pyridine-3-yl)methoxycarbonyl-aminomethyl]-benzamide Polymorphs and of the Amorphous Phase by X-Ray Powder Diffraction The X-ray powder diffraction data were recorded at room temperature using germanium-monochromatized CuKα1-radiation (λ=1.5406 Å). The 2Theta scans were performed using the small linear position sensitive detector with an angular resolution of 0.08° between 3°≤2Theta≤35° (step-width 0.5°), at room temperature.

The 2 Theta values of the strongest reflections of the three polymorphs in the X-ray powder pattern are given in the following Table 2.

TABLE 2

| Polymorph A | Polymorph B | Polymorph C |
|---|---|---|
| 18.4 | 9.2 | 17.7 |
| 18.8 | 18.1 | 18.4 |
| 19.1 | 19.4 | 18.8 |
| 20.9 | 20.0 | 19.2 |
| 22.6 | 20.4 | 20.0 |

TABLE 2-continued

| Polymorph A | Polymorph B | Polymorph C |
|---|---|---|
| 26.4 | 21.1 | 22.0 |
| 26.7 | 22.1 | 22.3 |
| 27.2 | 25.8 | 23.2 |
| | 27.4 | 23.4 |

One of ordinary skill in the art will appreciate that an X-ray diffraction pattern may be obtained with a measurement error that is dependent upon the measurement conditions. In particular, it is generally known that intensities in an X-ray diffraction pattern may fluctuate depending upon crystal habitus of the material and measurement conditions employed. Additionally, a measurement error of diffraction angle Theta for a conventional X-ray diffraction pattern at a given temperature is typically about ±0.1°, and such degree of measurement error should be taken into account as pertaining to the diffraction angles. Consequently, any crystal form that provides X-ray diffraction patterns that is substantially identical as to those disclosed in the accompanying Figures falls within the scope of the present invention.

Example 4

Analysis of the N-(2-aminophenyl)-4-[N-(pyridine-3-yl)methoxycarbonyl-aminomethyl]-benzamide Polymorphs and the Amorphous Phase by FT-Raman Spectroscopy The FT-Raman spectra were recorded using a resolution of 2 and 64 sans at a laser power of 250 mW.

The results of the Raman analysis are shown in Table 3. The data show the wave numbers ($cm^{-1}$) of characteristic bands in the FT-Raman spectra of Polymorph A, Polymorph B and Polymorph C and the amorphous phase.

TABLE 3

| Wave number of characteristic FT-Raman bands ($cm^{-1}$) | | | |
|---|---|---|---|
| Polymorph A | Polymorph B | Polymorph C | Amorphous phase |
| 3061 | 3075 | 3076 | 3062 |
| 3048 | 3063 | 3050 | 1649 |
| 1613 | 1639 | 1629 | 1613 |
| 1262 | 1613 | 1613 | 1598 |
| 1041 | 1328 | 1329 | 1322 |
| 1034 | 1299 | 1311 | 1256 |
| 936 | 1293 | 1297 | 1041 |
| 908 | 1040 | 1040 | 907 |
| 893 | 1033 | 908 | 776 |
| 776 | 916 | 783 | |
| | 902 | 775 | |
| | 778 | | |

According to a person ordinary skilled in the art, the acceptable tolerance for the wave number shift is ±2 $cm^{-1}$ dependent on the used equipment and measurements conditions. Consequently, any solid state form that provides a FT-Raman spectra that is substantially identical as to those disclosed in the accompanying Figures falls within the scope of the present invention.

Example 5

Analysis of the N-(2-aminophenyl)-4-[N-(pyridine-3-yl)methoxycarbonyl-aminomethyl]-benzamide Polymorph B by IR Spectroscopy The IR spectra of the polymorph B were recorded using diffuse reflection (KBr) and ATR. The major infrared bands and their assignments are summarized in the following Table 4.

TABLE 4

| Wave number of characteristic IR bands of polymorph B ($cm^{-1}$) | |
|---|---|
| KBr | ATR |
| 3349, 3311, 3216 | 3349, 3309 |
| 1705 | 1702 |
| 1641 | 1638 |
| 1262 | 1260 |
| 751 | 749 |

According to a person ordinary skilled in the art, the acceptable tolerance for the wave number shift is ±2 $cm^{-1}$ dependent on the used equipment and measurements conditions. Consequently, any solid state form that provides a FT-Raman spectra that is substantially identical as to those disclosed in the accompanying Figures falls within the scope of the present invention.

Example 6

Biological Activity of the N-(2-aminophenyl)-4-[N-(pyridine-3 yl)methoxy-carbonylaminomethyl]-benzamide Polymorph B in the DU-145 Human Prostate Carcinoma Model in Nude Mice Nude mice were orally treated after tumor transplantation with 10, 20 or 30 mg/kg of N-(2-aminophenyl)-4-[N-(pyridine-3 yl)methoxy-carbonylaminomethyl]-benzamide polymorph B. The active compound was applied in 30% HPβCD. As control, a vehicle of DMSO/ethanol 1.1 in 0.085% Myrj/NaCl/30% HPβCD was used. The tumor growth was determined after 27 to 56 days after tumor transplantation.

The results of that experiment are shown in FIG. 8.

According to the results, one can see that there is a clear inhibition with regard to the tumor growth if N-(2-aminophenyl)-4-[N-(pyridine-3 yl)methoxy-carbonyl-aminomethyl]-benzamide polymorph B is applied.

Figure 1:
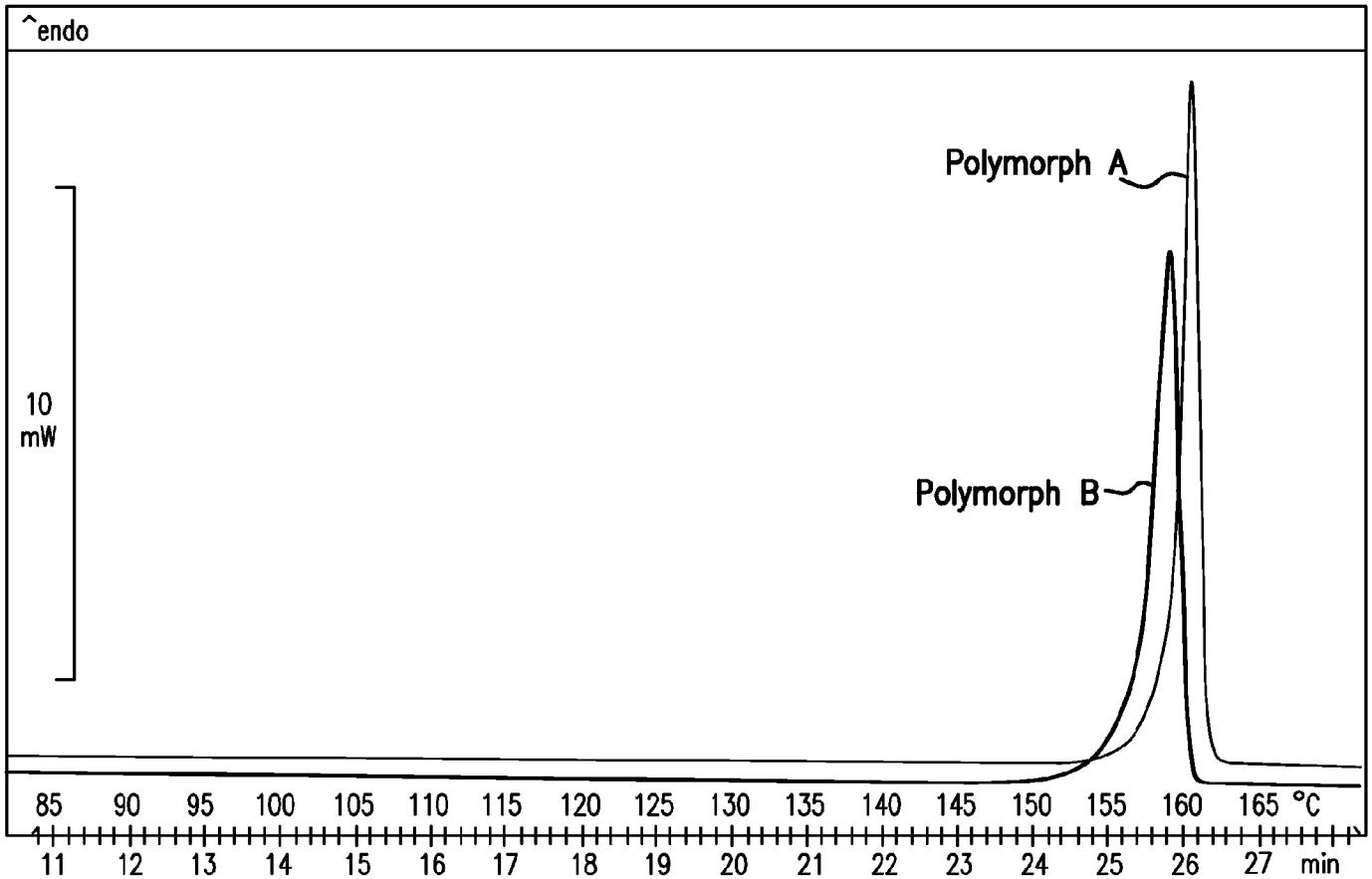
FIG. 1 shows a DSC trace of Polymorph A and Polymorph B of N-(2-aminophenyl)-4-[N-(pyridine-3-yl)methoxycarbonylaminomethyl]benzamide (MS-275).
Figure 2:
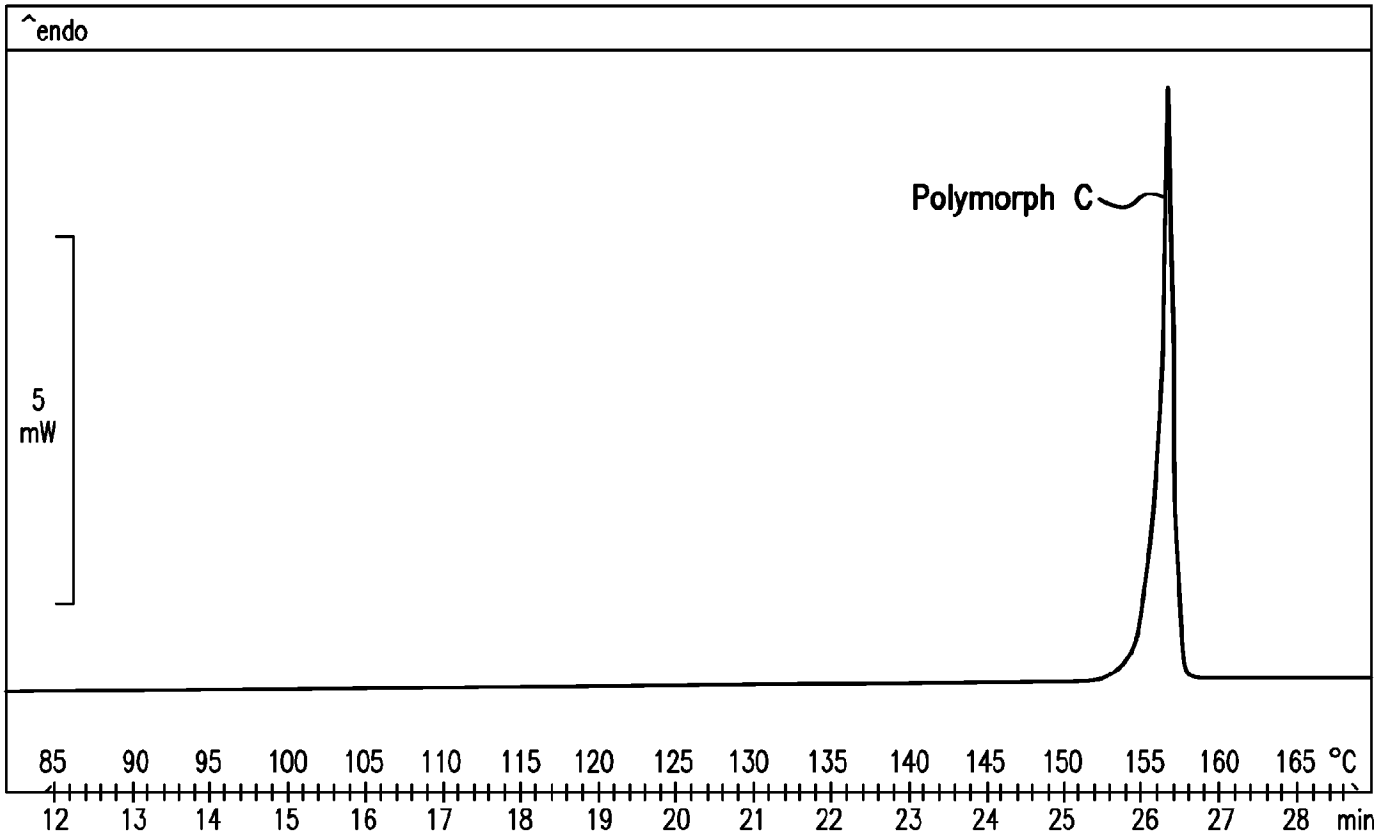
FIG. 2 shows a DSC trace of Polymorph C of N-(2-aminophenyl)-4-[N-(pyridine-3-yl)methoxycarbonylaminomethyl]benzamide (MS-275).
Figure 3:
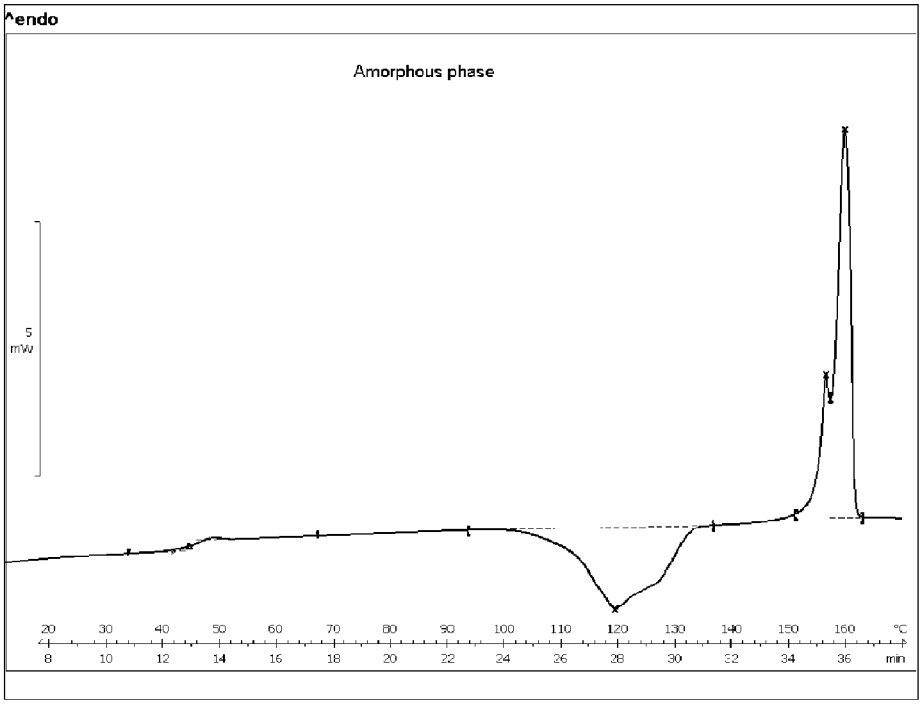
FIG. 3 shows a DSC trace of the amorphous phase of N-(2-aminophenyl)-4-[N-(pyridine-3-yl)methoxycarbonylaminomethyl]benzamide (MS-275).
Figure 4:
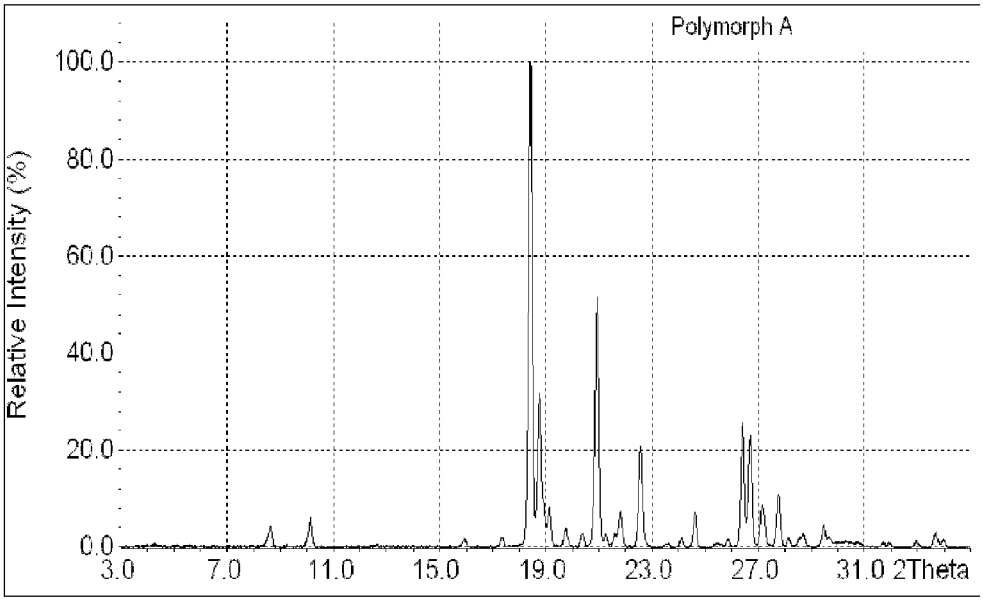
FIG. 4 shows the X-ray powder diffraction pattern of Polymorph A of N-(2-aminophenyl)-4-[N-(pyridine-3-yl)methoxycarbonylaminomethyl]benzamide (MS-275).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European patent application No. 08163274.7, filed Aug. 29, 2008, and U.S. Provisional patent Application Ser. No. 61/093,046, filed Aug. 29, 2008, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. Crystalline N-(2-aminophenyl)-4-[N-(pyridine-3-yl)methoxycarbonylamino-methyl]-benzamide polymorph B of formula I (I)

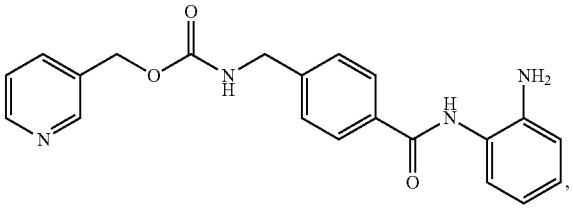

substantially free of N-(2-aminophenyl)-4-[N-(pyridine-3-yl)methoxy-carbonylamino-methyl]-benzamide polymorph A.

2. A process for preparing the crystalline N-(2-aminophenyl)-4-[N-(pyridine-3-yl)methoxycarbonylaminomethyl]-benzamide polymorph B compound of formula I (I)

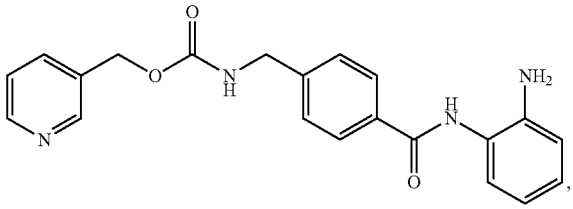

comprising a) dissolving crude N-(2-aminophenyl)-4-[N-(pyridine-3-yl)methoxy-carbonylaminomethyl]-benzamide in water and adding diluted hydrochloric acid to the resultant reaction mixture, at a constant internal reaction vessel temperature below 5° C., and b) adding charcoal to said reaction mixture and then stirring the reaction mixture for 1 to 20 hours at a temperature below 5° C., and c) filtering to remove the charcoal and rinsing with water, and d) while keeping the internal vessel temperature below 5° C. adjusting the pH of the reaction mixture to ≥8 with a diluted sodium hydroxide solution, and e) washing the resulting precipitated N-(2-aminophenyl)-4-[N-(pyridine-3-yl)methoxycarbonylaminomethyl]-benzamide with water and ethanol, and drying, and f) suspending the precipitate into a mixture of ethanol and water and heating up to a temperature of 40-90° C. for 1 to 10 hours, and g) after cooling down the mixture, rinsing the resulting precipitate with water and ethanol to give the pure N-(2-aminophenyl)-4-[N-(pyridine-3-yl)methoxycarbonylaminomethyl]-benzamide polymorph B which is subsequently dried at a temperature between 30-60° C.

3. A process according to claim 2, wherein steps b) and step c) are repeated.

4. Crystalline N-(2-aminophenyl)-4-[N-(pyridine-3-yl)methoxycarbonylamino-methyl]-benzamide polymorph B which is produced according to claim 2.

5. Crystalline N-(2-aminophenyl)-4-[N-(pyridine-3-yl)methoxycarbonylamino-methyl]-benzamide polymorph B according to claim 1, whose X-ray diffractogram has a reflection at 2Theta=21.1°.

6. Crystalline N-(2-aminophenyl)-4-[N-(pyridine-3-yl)methoxycarbonylamino-methyl]-benzamide polymorph B according to claim 1, whose X-ray diffractogram has reflections at 2Theta=21.1°, 20.4° and 27.4°.

7. Crystalline N-(2-aminophenyl)-4-[N-(pyridine-3-yl)methoxycarbonylamino-methyl]-benzamide polymorph B according to claim 1, whose Raman spectrum has a band at 902 $cm^{-1}$.

8. Crystalline N-(2-aminophenyl)-4-[N-(pyridine-3-yl)methoxycarbonylamino-methyl]-benzamide polymorph B according to claim 1, whose Raman spectrum has bands at 902 $cm^{-1}$, 3063 $cm^{-1}$, 1639 $cm^{-1}$ and 916 $cm^{-1}$.

9. Crystalline N-(2-aminophenyl)-4-[N-(pyridine-3-yl)methoxycarbonylamino-methyl]-benzamide polymorph B according to claim 1, whose IR spectrum (ATR) has bands at 1702 $cm^{-1}$, 3309 $cm^{-1}$, 1638 $cm^{-1}$, 1260 $cm^{-1}$ and 749 $cm^{-1}$.

10. Crystalline N-(2-aminophenyl)-4-[N-(pyridine-3-yl) methoxycarbonylamino-methyl]-benzamide polymorph B according to claim 1, whose IR spectrum (KBr) has bands at 1705 $cm^{-1}$, 3311 $cm^{-1}$, 1641 $cm^{-1}$, 1262 $cm^{-1}$ and 751 $cm^{-1}$.

11. Crystalline N-(2-aminophenyl)-4-[N-(pyridine-3-yl) methoxycarbonylamino-methyl]-benzamide polymorph B according to claim 1, whose X-ray diffractogram has a reflection at 2Theta=21.1°, 20.4° and 27.4° and the Raman spectrum has bands at 902 $cm^{-1}$, 3063 $cm^{-1}$, 1639 $cm^{-1}$ and 916 $cm^{-1}$, and the IR (ATR) spectrum has bands at 1702 $cm^{-1}$, 3311 $cm^{-1}$, 1641 $cm^{-1}$, 1262 $cm^{-1}$ and 751 $cm^{-1}$.

12. A method for treating a malignant tumor, an autoimmune disease, a dermatological disease or parasitism, comprising administering to a subject in need thereof an effective amount of N-(2-aminophenyl)-4-[N-(pyridine-3-yl)methoxycarbonylamino-methyl]benzamide polymorph B.

13. A pharmaceutical composition comprising N-(2-aminophenyl)-4-[N-(pyridine-3-yl)methoxy-carbonylaminomethyl]-benzamide polymorph B and a pharmaceutically acceptable diluent and/or carrier.

14. A pharmaceutical combination comprising N-(2-aminophenyl)-4-[N-(pyridine-3-yl)methoxy-carbonylaminomethyl]-benzamide polymorph B and one or more cytotoxic or cytolytic agents.

15. A method according to claim 12, wherein the N-(2-aminophenyl)-4-[N-(pyridine-3-yl)methoxy-carbonylaminomethyl]-benzamide polymorph B is administered together with a cytotoxic or cytolytic agent simultaneously, separately or sequentially.

16. Crystalline N-(2-aminophenyl)-4-[N-(pyridine-3-yl) methoxycarbonylamino-methyl]-benzamide polymorph B of formula I

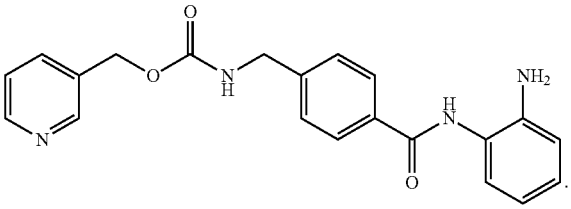

Figure 5:
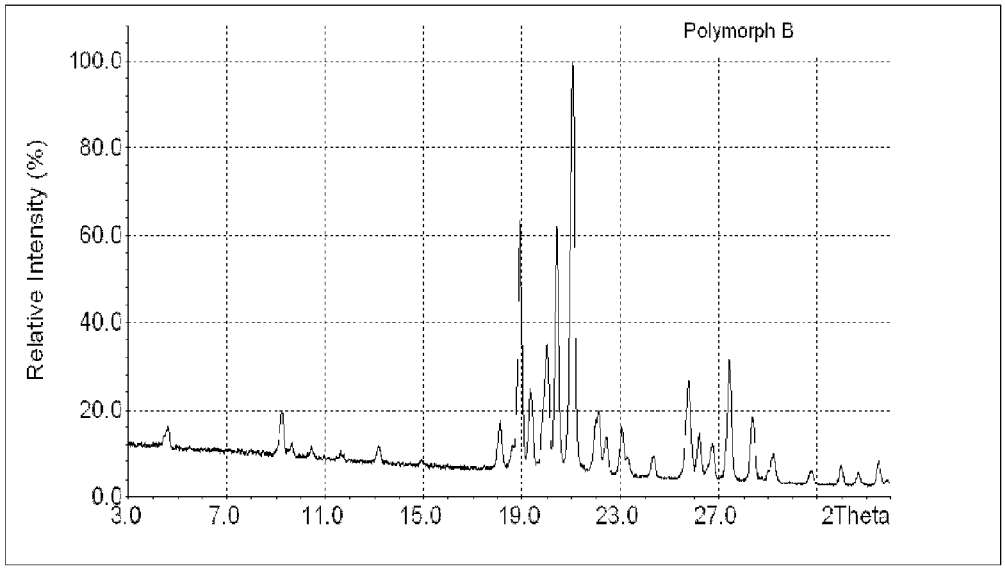
FIG. 5 shows the X-ray powder diffraction pattern of Polymorph B of N-(2-aminophenyl)-4-[N-(pyridine-3-yl)methoxycarbonylaminomethyl]benzamide (MS-275).
Figure 6:
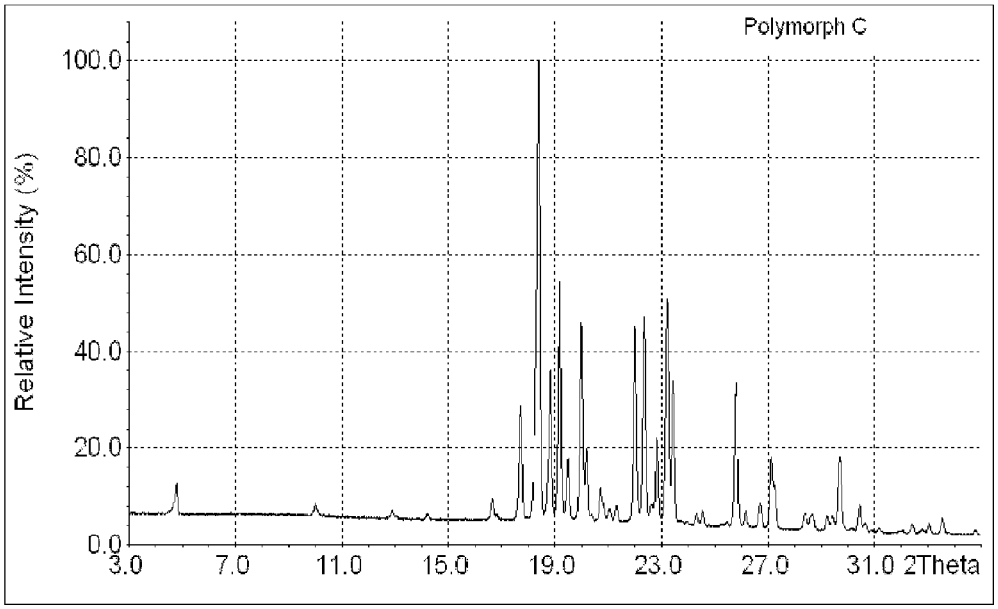
FIG. 6 shows the X-ray powder diffraction pattern of Polymorph C of N-(2-aminophenyl)-4-[N-(pyridine-3-yl)methoxycarbonylaminomethyl]benzamide (MS-275).
Figure 7:
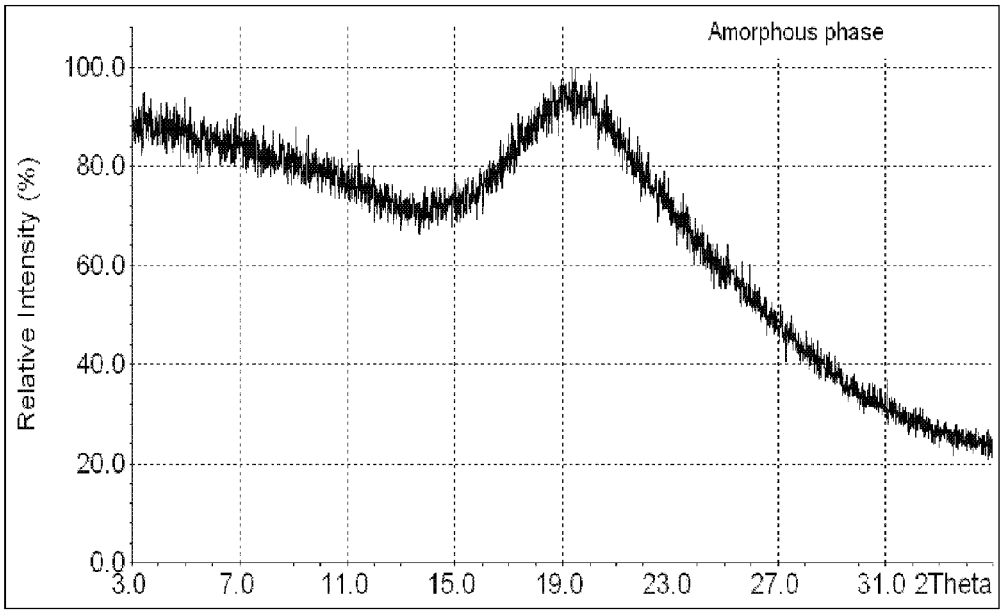
FIG. 7 shows the X-ray powder diffraction pattern of the amorphous phase of N-(2-aminophenyl)-4-[N-(pyridine-3-yl)methoxycarbonylaminomethyl]benzamide (MS-275).
Figure 8:
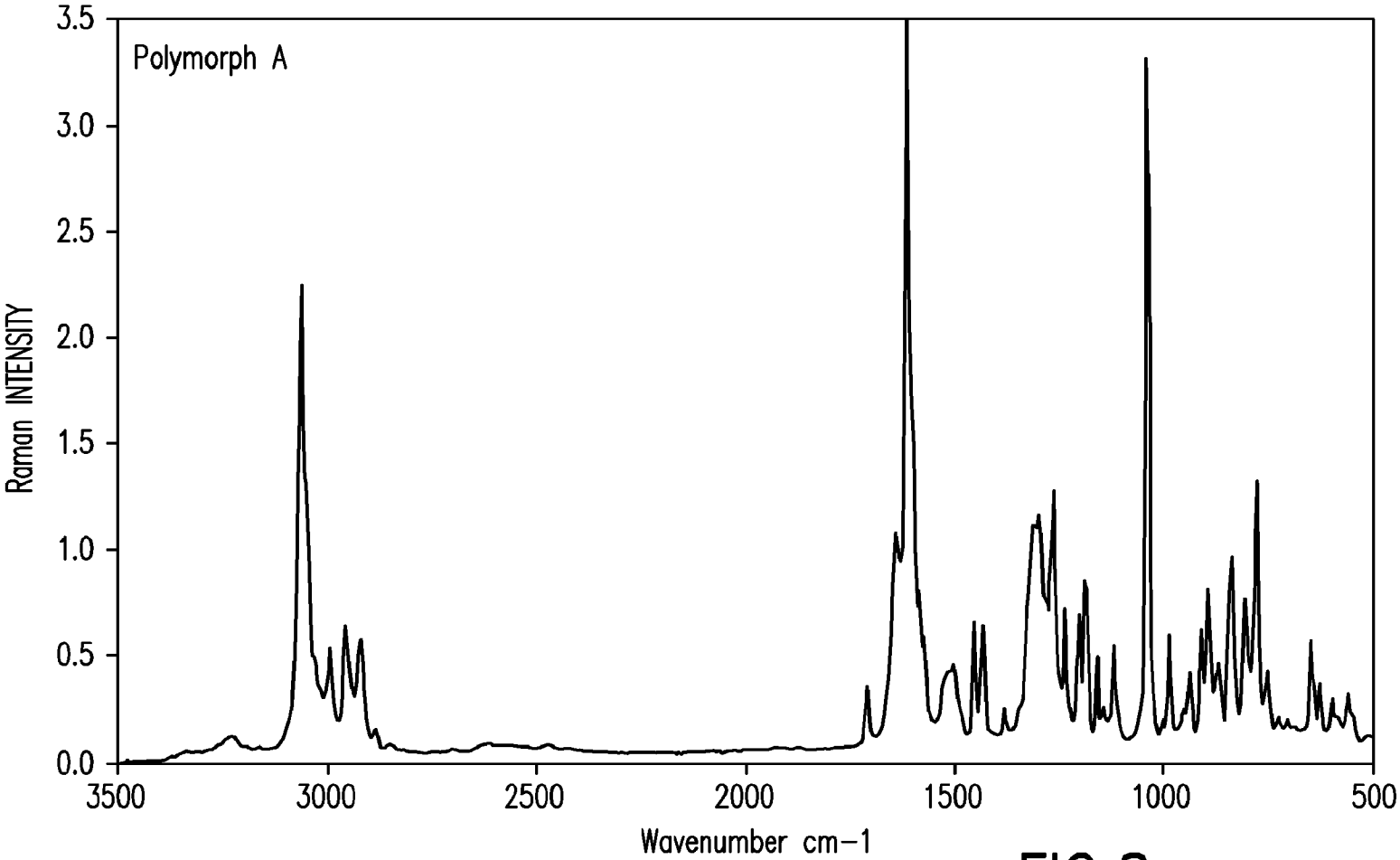
FIG. 8 shows the FT-Raman spectrum of Polymorph A of N-(2-aminophenyl)-4-[N-(pyridine-3-yl)methoxycarbonylaminomethyl]benzamide (MS-275).

17. Crystalline N-(2-aminophenyl)-4-[N-(pyridine-3-yl) methoxycarbonylamino-methyl]-benzamide polymorph B according to claim 16, whose X-ray diffractogram corresponds to FIG. 5.

18. Crystalline N-(2-aminophenyl)-4-[N-(pyridine-3-yl) methoxycarbonylamino-methyl]-benzamide polymorph B according to claim 1, whose X-ray diffractogram corresponds to FIG. 5.

Figure 9:
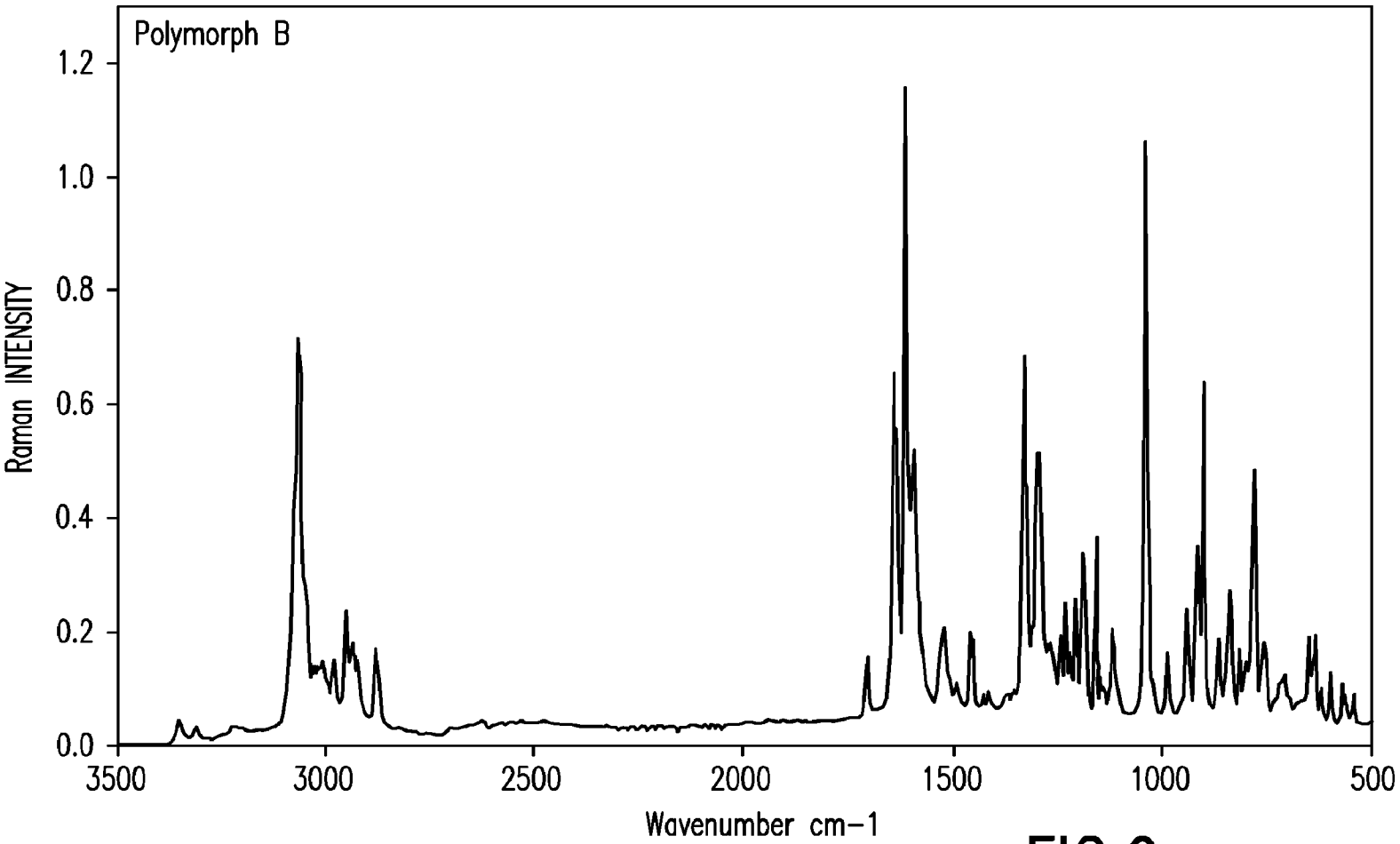
FIG. 9 shows the FT-Raman spectrum of Polymorph B of N-(2-aminophenyl)-4-[N-(pyridine-3-yl)methoxycarbonylaminomethyl]benzamide (MS-275).
Figure 10:
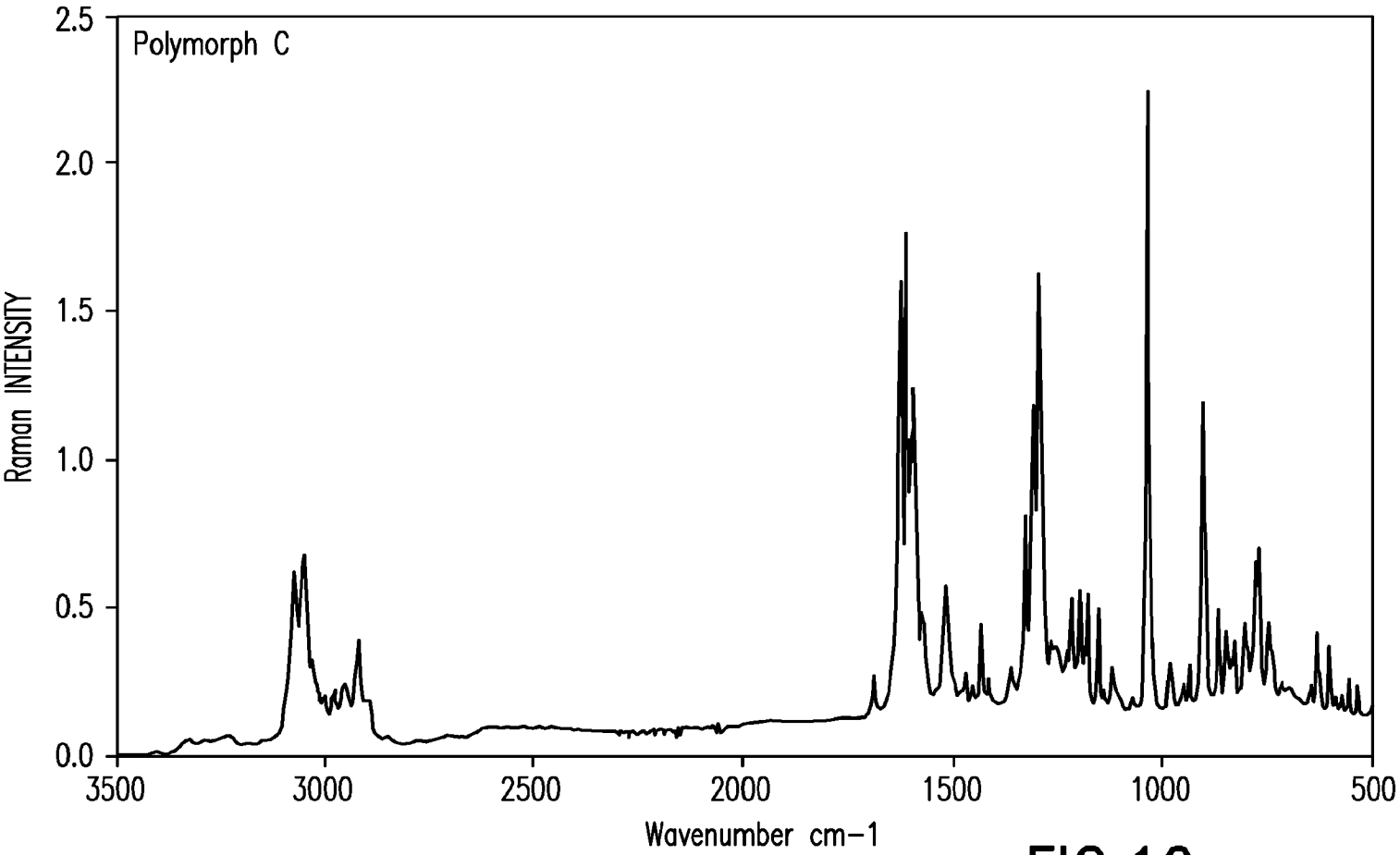
FIG. 10 shows the FT-Raman spectrum of Polymorph C of N-(2-aminophenyl)-4-[N-(pyridine-3-yl)methoxycarbonylaminomethyl]benzamide (MS-275).
Figure 11:
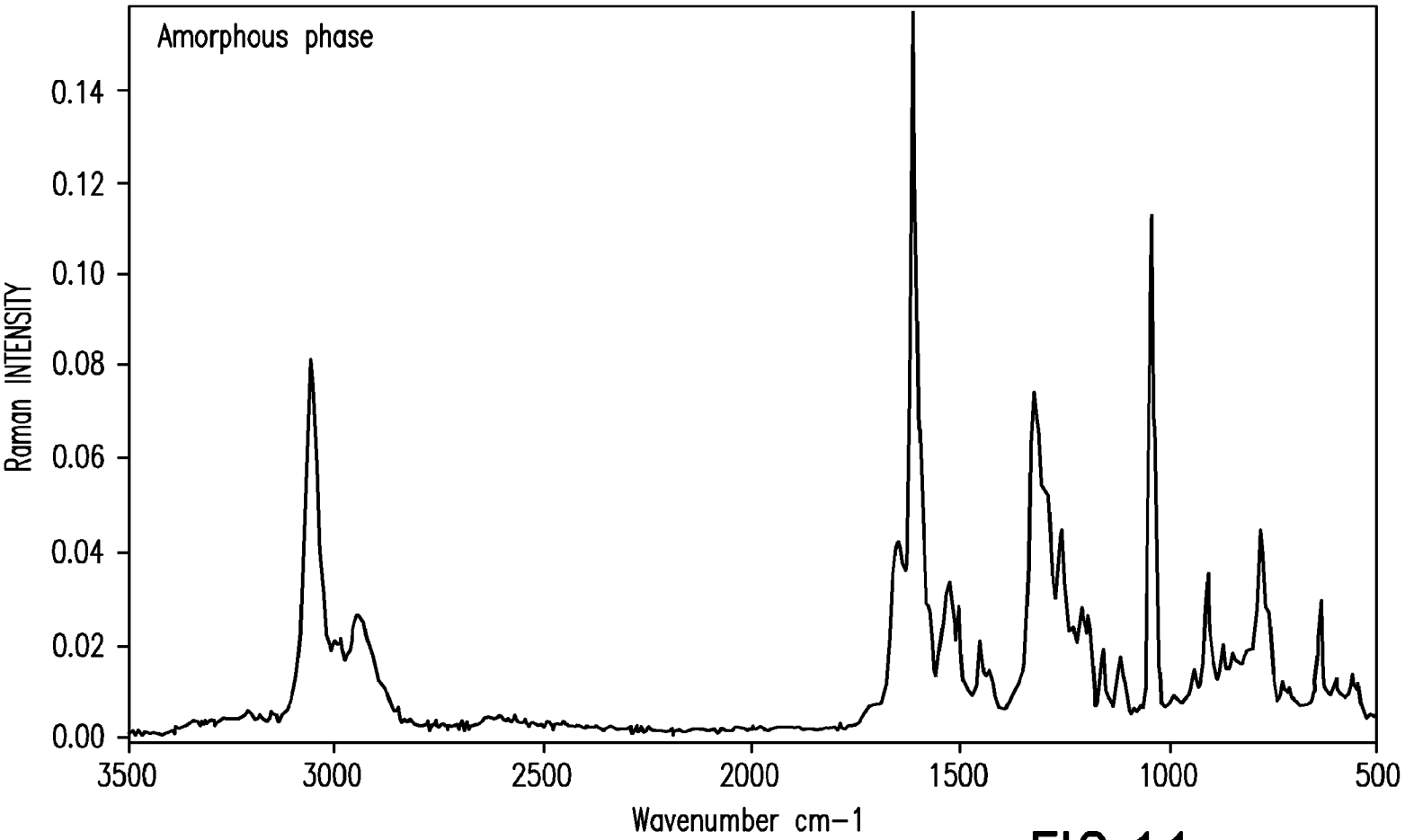
FIG. 11 shows the FT-Raman spectrum of the amorphous phase of N-(2-aminophenyl)-4-[N-(pyridine-3-yl)methoxycarbonylaminomethyl]benzamide (MS-275).

19. Crystalline N-(2-aminophenyl)-4-[N-(pyridine-3-yl) methoxycarbonylamino-methyl]-benzamide polymorph B according to claim 1, whose Raman spectrum corresponds to FIG. 9.

Figure 13:
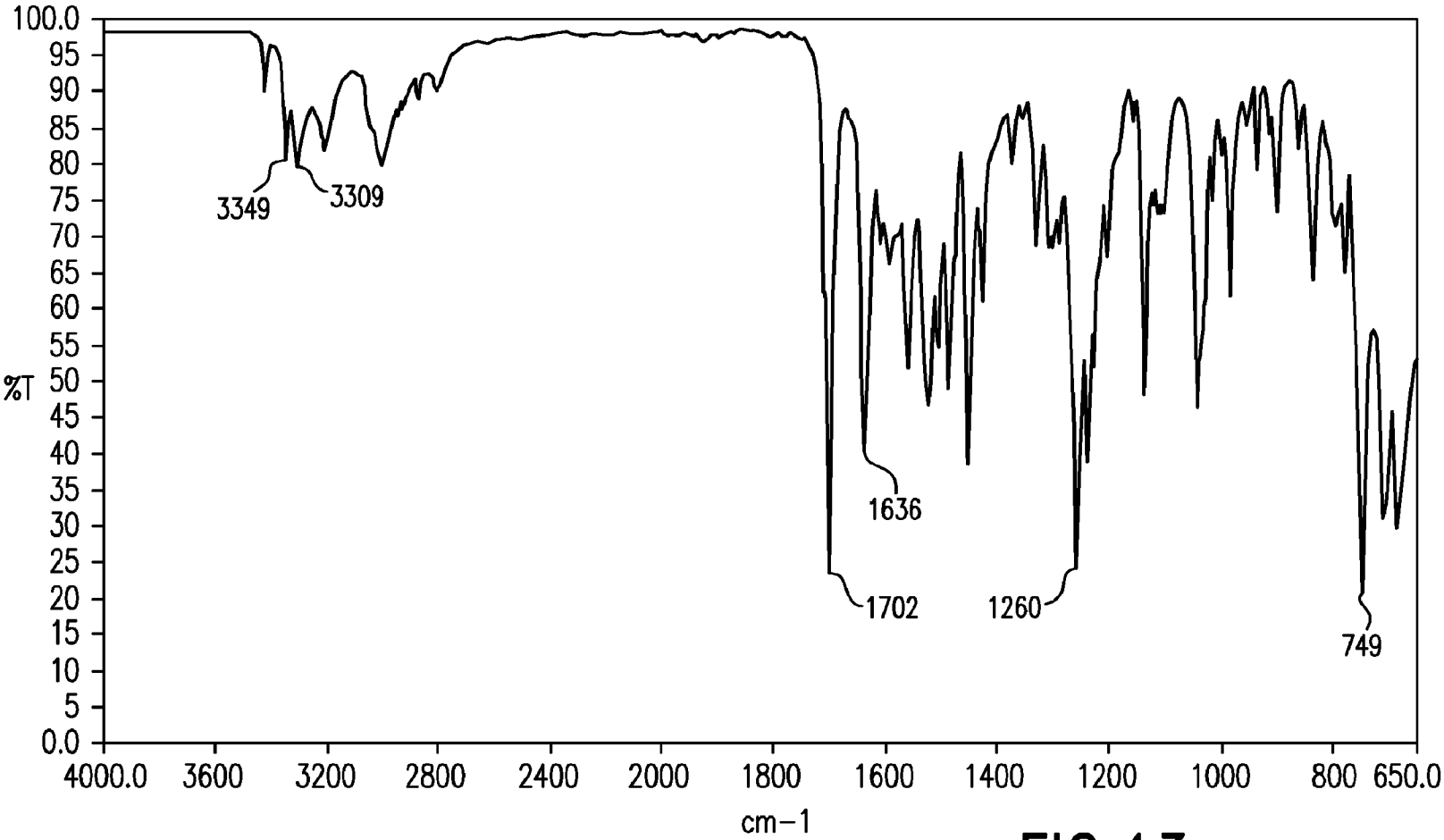
FIG. 13 shows the IR spectrum (ATR) of Polymorph B of N-(2-aminophenyl)-4-[N-(pyridine-3-yl)methoxycarbonylaminomethyl]benzamide (MS-275), and the major infrared bands and their assignments.
Figure 14:
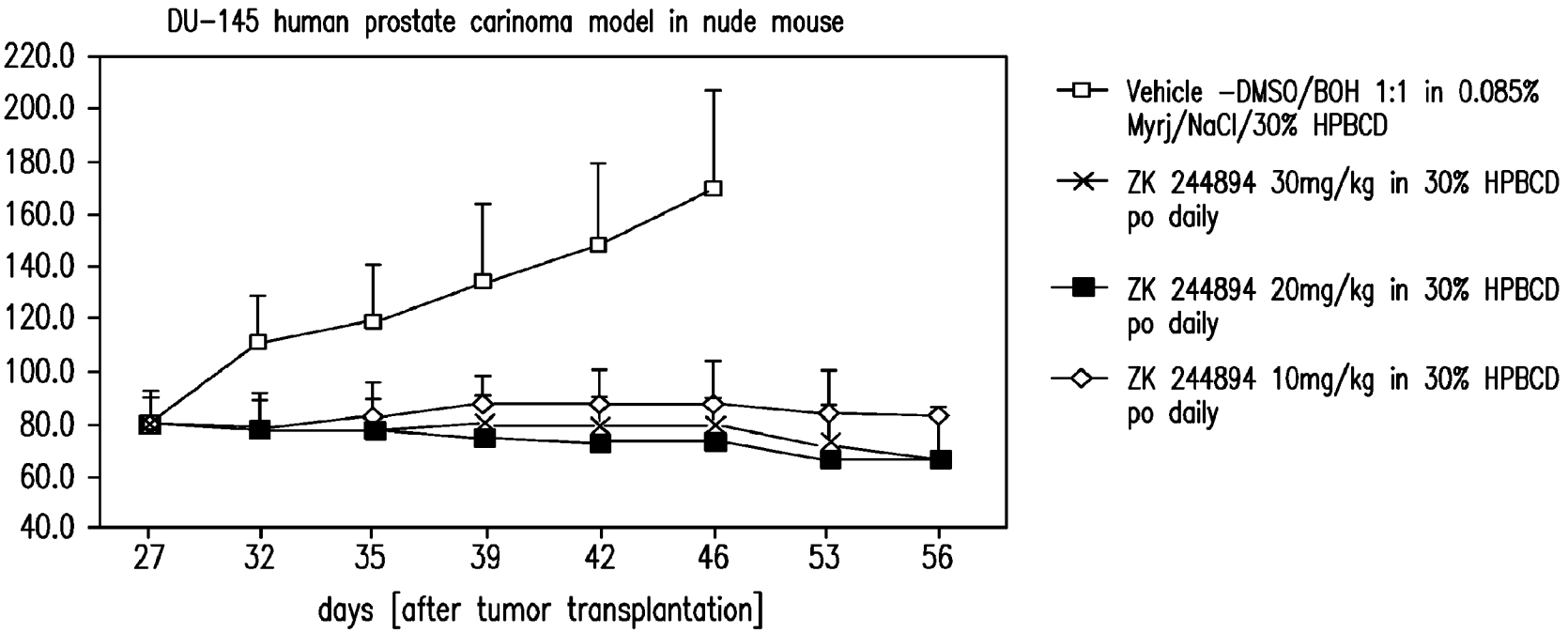
FIG. 14 shows the biological activity of the inventive Polymorph B of N-(2-aminophenyl)-4-[N-(pyridine-3-yl)methoxycarbonylaminomethyl]benzamide (MS-275) (ZK 244894), applied in different concentrations against a control (Vehicle-DMSO).

20. Crystalline N-(2-aminophenyl)-4-[N-(pyridine-3-yl) methoxycarbonylamino-methyl]-benzamide polymorph B according to claim 1, whose IR spectrum (ATR) corresponds to FIG. 13.

Figure 12:
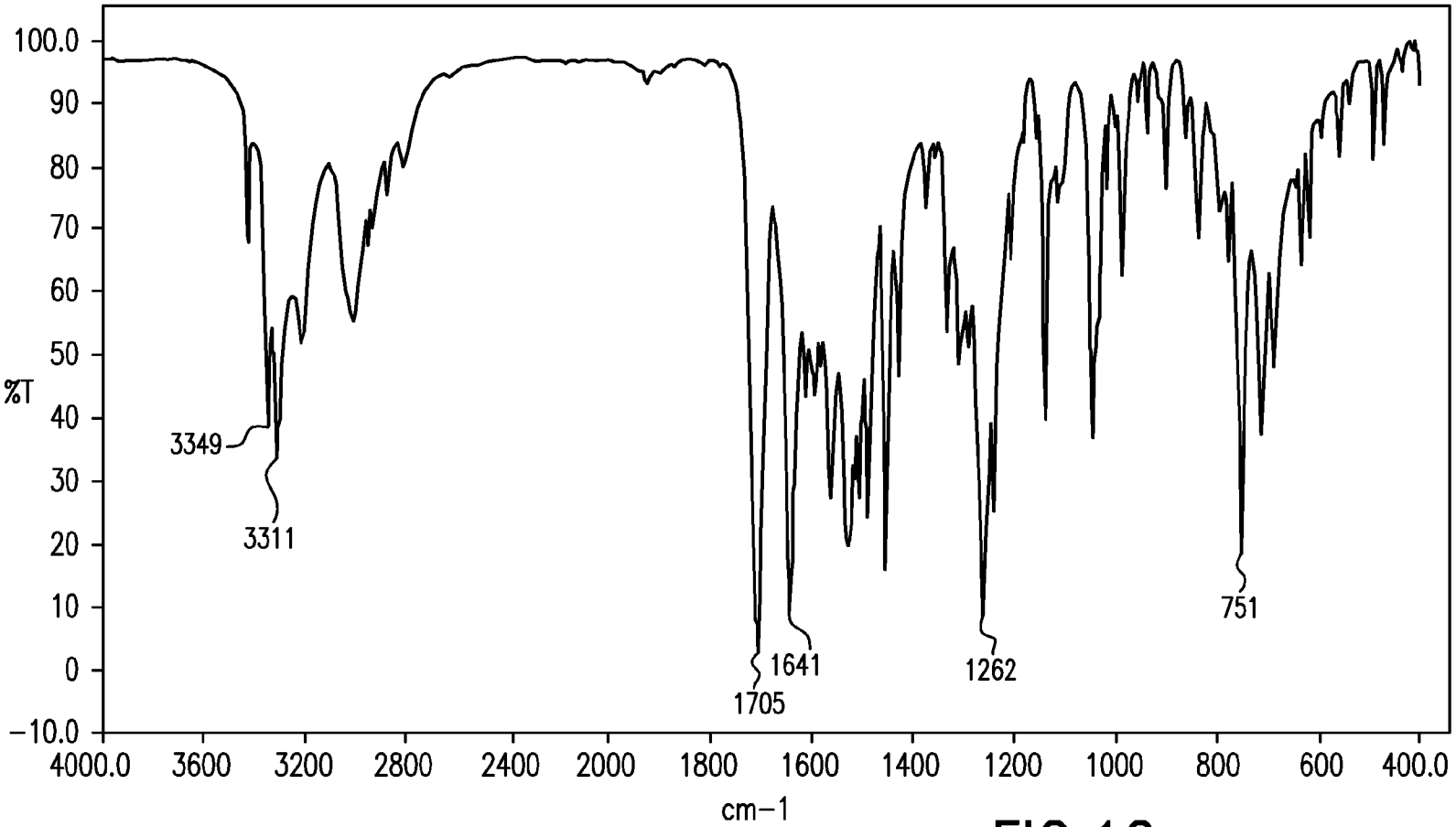
FIG. 12 shows the IR spectrum (KBr) of Polymorph B of N-(2-aminophenyl)-4-[N-(pyridine-3-yl)methoxycarbonylaminomethyl]benzamide (MS-275), and the major infrared bands and their assignments.

21. Crystalline N-(2-aminophenyl)-4-[N-(pyridine-3-yl) methoxycarbonylamino-methyl]-benzamide polymorph B according to claim 1, whose IR spectrum (KBr) corresponds to FIG. 12.

* * * * *